United States Patent [19]
McCann et al.

[11] 3,987,362
[45] Oct. 19, 1976

[54] SENSORS

[75] Inventors: John David McCann; Michael John Poole, both of Abingdon, England

[73] Assignee: United Kingdom Atomic Energy Authority, England

[22] Filed: Oct. 25, 1974

[21] Appl. No.: 518,183

[30] Foreign Application Priority Data
Nov. 12, 1973  United Kingdom............. 52492/73

[52] U.S. Cl............................. 324/30 A; 324/65 R
[51] Int. Cl.².......................................... G01N 27/72
[58] Field of Search............ 324/30 R, 65, 29, 30 A

[56] References Cited
UNITED STATES PATENTS

| | | | |
|---|---|---|---|
| 2,435,043 | 1/1948 | Lehde et al............................ | 324/30 |
| 3,387,209 | 6/1968 | Eames et al.......................... | 324/30 |
| 3,855,522 | 12/1974 | Kobayashi............................. | 324/30 |

Primary Examiner—John Kominski
Attorney, Agent, or Firm—Larson, Taylor and Hinds

[57] ABSTRACT

A device for monitoring the electrical conductivity of an electrically conductive fluid comprising at least two electrical coils for immersion in the fluid. One of the coils constitutes a coil to be energized with an alternating current and the other in use constitutes a detection coil. The coils are arranged relative to one another so that in use they are mutually inductively coupled and are inductively coupled by the fluid.

An electronic circuit is provided which includes a power supply for supplying an alternating current to the coil or coils to be energized, and a detector for detecting the voltage induced in the detection coil or coils. The detector provides an indication of changes in the inductive coupling between the coil or coils to be energized and the detection coil or coils.

22 Claims, 6 Drawing Figures

SENSORS

This invention relates to sensors for detecting the conductivity of an electrically conductive fluid in which the sensor is immersed. Such sensors may be used to monitor the temperature of fluids the conductivity of which varies as a result of temperature fluctuations and also for detecting fluctuations in the flow rate of such fluids.

In known liquid-metal cooled nuclear reactors, fuel is arranged in sub-assemblies which are disposed in the coolant flow path so that coolant streams flow in parallel over the fuel to cool it. In a prototype fast reactor there are as many as 450 sub-assemblies each of which contains up to 64 fuel pins. A blockage in one of these coolant streams can cause overheating of the fuel and it is desirable that the reactor operator should receive early warning of such a blockage.

There is a need to monitor the temperature of the coolant, or at least variations in temperature from a predetermined value, before the coolant leaves the confines of the sub-assembly and mixes with the outlet streams of the other sub-assemblies.

Random mixing of a number of coolant streams at slightly different temperatures produces temperature fluctuations about a mean value and this gives rise to a fluctuating signal, conveniently referred to as "fuel temperature noise". It is believed that blockage of one coolant stream has a greater relative effect on this fluctuating signal than on the mean outlet temperature of the coolant. The time constant of the signal is however, of the order of only a few milliseconds and in conventional measurements of the temperature fluctuations using thermocouples all the higher frequency components of temperature noise, due to mixing of coolant streams of different temperatures, are lost. Furthermore the thermal capacity of the thermocouples and their electrical insulation are important limiting factors. Also, thermocouples detect the low frequency components of "inlet temperature noise" and "reactor power temperature noise" produced by variations in inlet temperature and fluctuations of reactor power respectively.

British Pat. No. 1,252,257 discloses a conductivity sensor which is capable of measuring the high frequency components of temperature noise and which is suitable for detecting changes in the electrical conductivity of the liquid metal coolant which result from temperature changes. The conductivity sensor described in the above mentioned British Patent employs two pairs of energised coils which are immersed in the conductive liquid metal coolant. The coils of one pair are connected in a series-aiding manner and the pair constitute a sensor-coil assembly, and the coils of the other pair are connected in a series-opposing manner and this pair constitutes a compensating coil assembly in the form of a non-inductive bifilar coil which compensates for circuit impedance changes. The sensor coil assembly is connected in electrical series with a variable inductor and a unity ratio bridge circuit and the compensating coil assembly forms the reference arm of the bridge circuit. A power supply is provided to energise the bridge and means are provided to detect when the bridge is in a null-condition. The sensor coil assembly and the compensating coil assembly are not mutually inductively coupled. The electronic detection circuit required for each sensor of the type described in British Pat. No. 1,252,257 is, however, too complex to permit the use of such sensors in large numbers as would be required for individual monitoring of each fuel channel in a nuclear reactor.

According to the present invention there is provided a device for monitoring the electrical conductivity of an electrically conductive fluid comprising at least two electrical coils for immersion in the fluid, one of the coils constituting a coil to be energised with an alternating current and the other in use constituting a detection coil, the coils being arranged relative to one another so that in use they are mutually inductively coupled and are inductively coupled by the fluid, and an electronic circuit which includes a power supply for supplying an alternating current to the coil or coils to be energised, and a detector for detecting the voltage induced in the detection coil or coils and for providing an indication of changes in the inductive coupling between the coil or coils to be energised and the detection coil or coils.

The device may comprise three coils positioned along a common axis one of which constitutes a coil to be energised and the other two constituting detection coils. In this case the coil to be energised is arranged co-axially with the detection coils and is positioned between the detection coils. Alternatively, a single detection coil may be arranged between two coils to be energised.

The device may comprise four coils positioned along a common axis two of which constitute coils to be energised and the other two constituting detection coils. The two detection coils may be located side-by-side along the axis and be positioned between the coils to be energised. In this latter case the detection coils may be connected together in electrical series, and if desired, in the case where there are two coils to be energised they may be connected together in electrical series.

Preferably the electronic circuit includes means for generating a reference signal with which the current supplied to the coil or coils to be energised can be compared. The means for generating the reference signal may comprise a feed back circuit which is operative in response to variations from a predetermined relationship between the reference signal and the electrical current supplied to the coil or coils to be energised to tend to reduce variations in the electrical current supplied to the coil or coils to be energised from the said predetermined relationship. The feed-back circuit may further comprise means for deriving an alternating signal indicative of the current supplied to the coil or coils to be energised, a first rectifying circuit for rectifying the said alternating signal, a first integrating amplifier for generating an output signal which is the integral of the output signal from the first rectifying circuit with respect to time, and a variable gain controlled amplifier which, in response to the output signal from the first integrating amplifier, is operative to adjust the current supplied to the coil or coils to be energised.

Preferably a first non-integrating amplifier is provided for amplifying the output signal of the first rectifying circuit, and the first non-integrating amplifier is connected in parallel with the first integrating amplifier. The said first integrating amplifier may be an inverting amplifier and the said first non-integrating amplifier is a non-inverting amplifier. Alternatively the said first integrating amplifier is a non-inverting amplifier and the said first non-integrating amplifier is an inverting amplifier.

The electronic circuit may further include a comparator circuit for comparing the current supplied to the coil or coils to be energised with a signal indicative of the voltage induced in the detection coil or coils, and for producing an output signal indicative of the difference between the current supplied to the coil or coils to be energised and the signal produced by the detection coil or coils. The comparator circuit may comprise in electrical series, means for receiving the signal produced by the detection coil or coils, a second rectifying circuit for rectifying the signal produced by the detection coil and a second integrating amplifier for generating an output signal which is the integral of the output signal from the first rectifier circuit with respect to time.

A second non-integrating amplifier may be connected in parallel with the second integrating amplifier, in this case, either the said second integrating amplifier is an inverting amplifier and the said second non-integrating amplifier is a non-inverting amplifier, or the said second integrating amplifier is a non-inverting amplifier and the said second non-integrating amplifier is an inverting amplifier.

The electronic circuit may include means for comparing the output signals of the said first non-integrating amplifier and said first integrating amplifier with a signal representative of the difference between the output signals of the said second non-integrating amplifier and said second integrating amplifiers, to produce an output signal representative of the relationship between changes of the current supplied to the coil or coils to be energised and changes of the signal produced by the detection coil or coils relative to predetermined mean values.

The electronic circuit may further include means for comparing the output signal of the first integrating amplifier with the output signal of the second integrating amplifier and for providing an indication of the relationship between the mean levels of the current supplied to the energised coil or coils and the mean signal produced by the detection coil or coils.

The electronic circuit may include means for comparing the output signal of the second integrating amplifier with the output signal of the second non-integrating amplifier for providing an indication of the relationship between the mean level of the signal indicative of the voltage induced in the detection coil or coils and fluctuations of the signal indicative of the voltage induced in the detection coil or coils.

The electronic circuit may include means for comparing the output signal of the first non-integrating amplifier with the output of the second non-integrating amplifier for providing an indication of the relationship of variations of the current supplied to the coil or coils and variations of the output signal of the detection coil or coils.

In the case where the device has two detection coils, the detection coils may be arranged so as to provide a push-pull input to two amplifier channels. In this case each of the amplifier channels comprises a variable gain controlled amplifier, and a rectifier circuit for rectifying the output signal of the variable gain controlled amplifier. Each of the detection coils is connected to an input of one of the variable gain controlled amplifiers, and the output of each of the channels is connected to an input of a differential amplifier which is common to both channels. The differential amplifier being operative to compare the output signal of the channels and produce an output signal which is used to alter the gain of the variable gain controlled amplifier of each channel in response to the output signal of the differential amplifier.

Preferably means are provided for generating a reference signal with which the output signal of the differential amplifier is compared, and means are provided for producing a signal, indicative of the difference between the reference signal and the output signal of the differential amplifier, which is used to control the gain of the variable gain controlled amplifier of each channel.

The output signal of each channel may be fed to a potential dividing circuit so that a signal indicative of the difference between the output signals of each channel is produced. The signal indicative of the difference between the output signals of each channel is preferably fed to the input terminal of an integrating amplifier and a non-integrating amplifier.

The output signal of the integrating amplifier and the output signal of the non-integrating amplifier are preferably fed to a potential dividing circuit so that a signal representative of the difference between the output signals of the integrating and non-integrating amplifiers is produced.

Where a plurality of detection coils, or energised coils are provided, the location of the energised coil or coils relative to the detection coil or coils, and the inductive coupling between them may be arranged such that the electrical conductivity of the fluid is monitored at two or more regions.

One or more devices so constructed may be used to monitor the electrical conductivity of a flowing stream at two regions, one of which is upstream of the other, for example to measure the temperature of the fluid. In this case, means may be provided for discriminating between changes in electrical conductivity of the fluid due to temperature changes, and magnetic flux distortions, affects of inductance, and reflected impedance of the fluid, due to variations in the flow rate of the fluid.

The result of variations of flow rate will show up as an "apparant" change in the electrical conductivity of the fluid but in reality the variation in flow rate does not in fact, alter the electrical condictivity of the fluid but rather it alters the inductive coupling between the fluid and the detection coil or coils and distorts the magnetic flux generated in the vicinity of the detection along the line of flow.

To discriminate between changes in detector coil voltage due either to temperature changes or changes in flow rate of the fluid, the detection coil or coils may be arranged relative to the energised coil or coils such that the flow of the fluid serves to enhance the coupling between the energised coil and a first detection coil but serves to diminish the coupling between the energised coil and a second detection coil. In this case, by adding the outputs of the two detection coils the effect of flow rate of the fluid can be cancelled. On the other hand by subtracting the output of one detection coil from the other detection coil the combined changes in flow rate and temperature may be determined.

According to a further aspect of the present invention there is provided a temperature sensor for monitoring the temperature of a liquid-metal coolant flow in a nuclear reactor by monitoring changes in the electrical conductivity of the coolant comprising a device constructed as aforesaid.

According to a further aspect of the present invention there is provided a method of monitoring the electrical conductivity of an electrically conductive fluid comprising the steps of locating two coils in the fluid such that the coils are mutually inductively coupled and are inductively coupled by the fluid, energising one of the coils with an alternating current and detecting the output from in such a manner as to detect variations in the fluid inductive coupling.

A number of embodiments of the invention will now be described by way of example, with reference to the drawings filed with the provisional in which.

Figure 1:
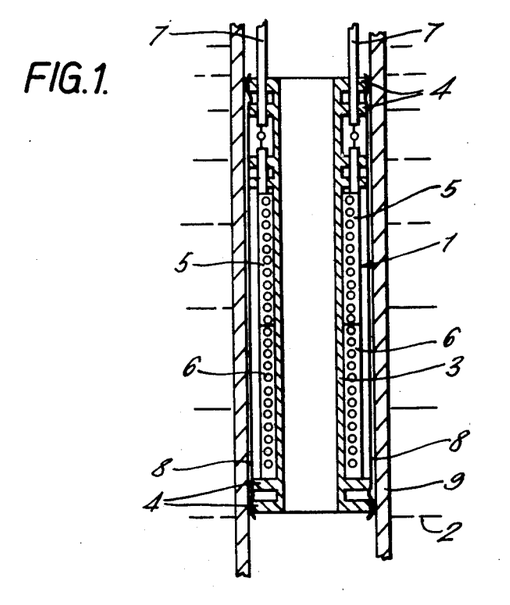
FIG. 1 illustrates one form of device constructed in accordance with the present invention for monitoring the electrical conductivity of an electrically conductive fluid.

Referring to FIG. 1 there is shown a device 1 for monitoring the electrical conductivity of an electrically conductive fluid 2 in which the device is immersed. The former 3 is constructed from stainless iron and comprises a tube 6 mms inside diameter, 7 mms outside diameter, 70 mms long (total length covered by the windings being about 50 mm). The former 3 is provided at its ends with flanges 4. On to the former 3 are wound coils 5 and 6 which are fabricated from ceramic or other high temperature insulation wire. A mineral insulated feed cable 7 is brazed or welded into the flanges 4 and their inner conductors are connected to the coils 5 and 6. The device so constructed, is covered with a thin stainless steel sheath 8 and the complete sensor is designed to operate inside a stainless steel thimble tube 9 which forms a physical barrier between the sensor and the electrically conductive fluid 2 which is typically liquid sodium at 600°C disposed around the outside of tube 9.

In operation of the device of FIG. 1, coil 5 is energised whilst coil 6 forms a detection coil; both coils 5, 6 are inductively coupled together and are inductively coupled by the electrically conductive fluid 2.

It will be seen that the fluid 2 effectively forms a single turn tertiary winding spanning the length of the former 3. Furthermore the voltage appearing across the detection coil 6 will depend upon the coupling factor between the coils 5 and 6 and the reflected effects of the fluid 2. When the coupling factor is made high, then high levels of coil voltage are obtained but the sensitivity to changes in the fluid 2 is low. Conversely, by employing weak coupling, the amplitude of the coil voltage can be made to change at a rate equal to the rate of change of resistivity of the surrounding fluid 2. However, with weak coupling, signal levels are low and better overall performance is obtained using a coupling which gives approximately half the ultimate sensitivity to resistivity changes. This optimum value of coupling appears to be in the range $K = 0.1$ to $0.3$ where $K$ is the coupling factor.

Figure 2:
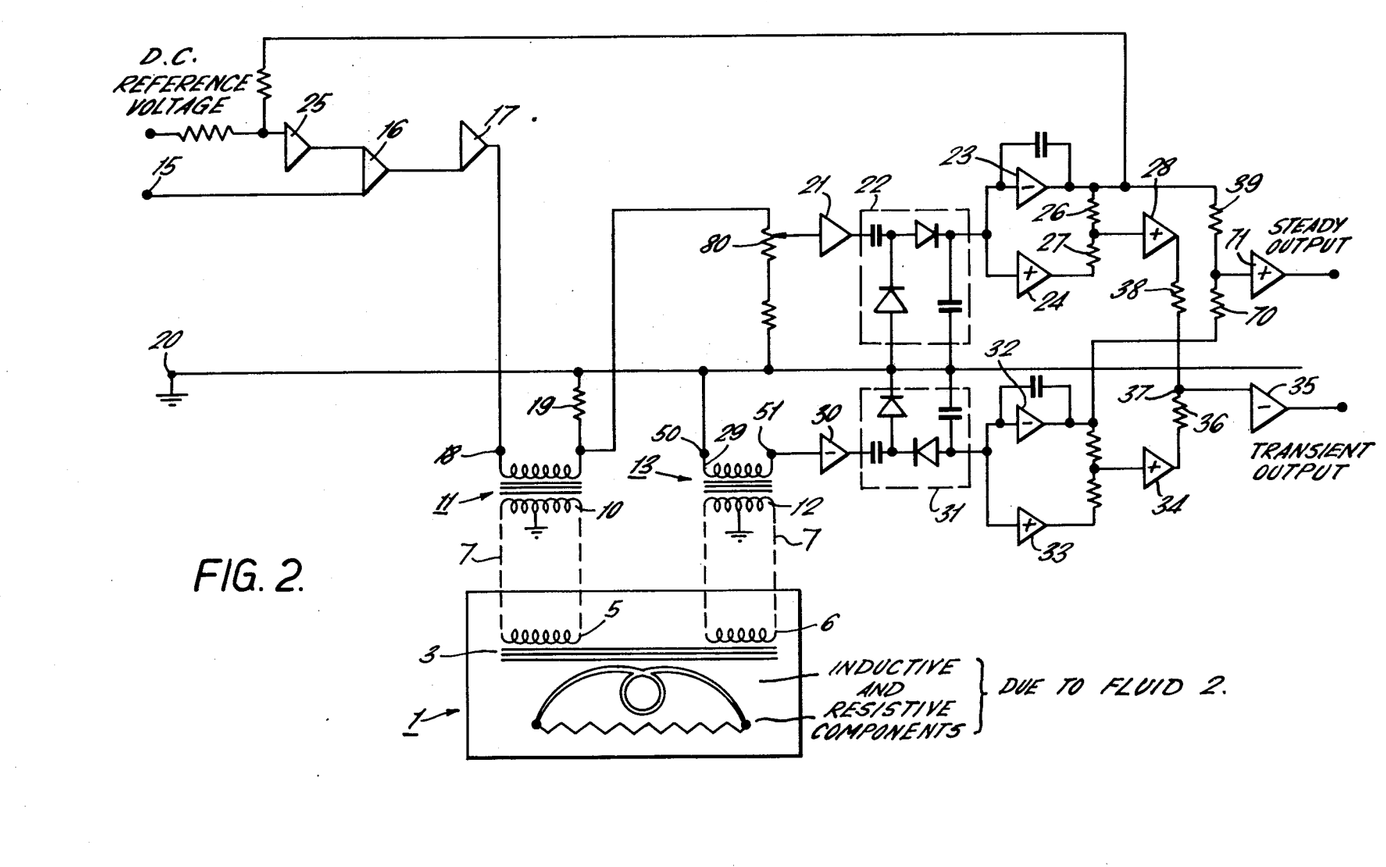
FIG. 2 is a circuit diagram of an electronic control system for use with the device of FIG. 1 and for use with the devices of FIGS. 3 to 5 for determining temperature only.

The electrical control circuit for the device of FIG. 1 is shown in FIG. 2. The device 1 is shown schematically, and the inductive and resistive components due to the surrounding conductive fluid 2 are also indicated schematically. The coil 5 is connected to a balanced secondary winding 10 of a transformer 11. Similarly, the detector coil 6 of the device 1 is connected to a balanced primary winding 12 of a transformer 13 by way of mineral insulated cables 7.

A stable source of alternating voltage (typically 1 kHz for sensors operating inside a 13 mm outside diameter thimble tube 9 surrounded by liquid sodium at 600°C) is applied to the input terminal 15 of variable gain controlled amplifier 16. The 1 kHz waveform is further amplified by a 3 watt integrated circuit power amplifier 17. The power level from the amplifier 17, typically 1 to 2 watts R.M.S., is applied to one end of a primary winding 18 of the transformer 11. A resistor 19 is connected in electrical series between the other end of the primary winding 18 and an earth connection 20. Since virtually all of the current flowing in the primary winding 18 of transformer 11 is due to driving the coil 5 of the device 1 the voltage developed across resistor 19 is proportional to the current flowing in the coil 5. The voltage appearing across resistor 19 is amplified by an amplifier 21, rectified by a rectifier circuit 22, and passed to the input of an inverting integrating amplifier 23 to produce a DC signal (representative of the current flowing in the coil 5) and to the input of a non-inverting non-integrating amplifier 24. The output of the amplifier 23 is fed-back and compared with a DC reference voltage, any errors between the voltage at the output of amplifier 23 and the reference voltage are amplified by an amplifier 25 and used to control the amplification of the amplifier 16. By closing the feed back loop, the voltage across resistor 19, and hence the current flowing through coil 5 of the device 1, are stabilized. The stabilized current level in the coil 5, typically 30 to 40 mA R.M.S., can be set by various means such as by the choice of the reference voltage, the value of resistance 19 or, for trimming purposes, by the adjustment of a variable resistor 80 which is connected in the input line to amplifier 21 between earth connection 20 and the junction between resistor 19 and the primary winding 18 of the transformer 11.

The output signal of the amplifier 24 is a steady DC level on which is superimposed signals indicative of short term fluctuations of the current in the coil 5 and common mode noise. Since amplifier 23 is an inverting amplifier, the output signal of amplifier 24 will be of the opposite sign to the output signal of amplifier 23. Hence, if two equal resistors, 26 and 27, are connected in series between the outputs of the amplifiers 23, 24 then these output signals can be compared and the difference signal at the junction between resistors 26, 27 can be amplified by an amplifier 28.

Since coil 6 is inductively coupled to coil 5 and to the electrically conductive fluid 2, the current flowing through coil 5 induces a voltage in coil 6. Coil 6 produces an output signal, typically 30 to 40 mV R.M.S., on the secondary winding 29 of the transformer 13. One side of the secondary winding 29 is connected to earth 20 whilst the other side is connected to an inverting amplifier 30 which amplifies the signal produced at the secondary winding 29 of transformer 13. The amplified signal is then rectified by the rectifier circuit 31 to produce an output DC level of about 8 volts on which are superimposed signals indicative of short term fluctuations in the electrical conductivity of the electrically conductive fluid 2. The amplifiers 21 and 30 are provided with frequency selective feed-back arranged to give maximum amplification at the driving frequency of 1 kHz. Although the Q (about 3) of the amplifiers is low, good rejection against both high and low frequency noise is obtained. The voltage at the output of rectifier circuit 31 will be almost directly proportional to the instantaneous temperature of the electrically conducting fluid 2, and the time resolution is a function of the drive frequency, physical size of the sensor, and the time constants of the whole electronic circuit. A typical time resolution of the system described may be of the order of 10 milliseconds. By increasing the driving frequency (at input 15) to about 4 kHz and appropriately changing the values of frequency selective elements of the circuits, resolution times of approximately 2 ms can be obtained.

The output signal from the rectifier circuit 31 is fed to the input of an inverting integrating amplifier 32 and a non-integrating, non-inverting amplifier 33. In this way, small but rapid fluctuations in temperature can be measured by subtracting the integrated and non-integrated signals and then amplifying the difference using amplifier 34 in a similar way to that described with reference to the amplifiers 23, 24 and 28.

The overall sensitivity of the transient temperature signals is such that 1% change in amplitude of the signal on the secondary winding 29 of the transformer 13 produces 6 volts change at the output of an amplifier 35.

To ensure that variations of ± 0.1% in signal amplitude can be detected with certainty, background noise has to be kept to a minimum. To achieve this, the difference signal at the output of the amplifier 34 is fed to the input 37 of the amplifier 35 by way of a resistor 36 connected in electrical series with the resistor 38 and the output of amplifier 28. In this way, variations in amplitude due to imperfections in the driving current, or common mode noise, are cancelled at the input of the amplifier 35 by the signals from the amplifier 28. The signals from amplifier 34 will be of the opposite sign to those from the amplifier 28.

Across the output of the integrating, inverting amplifiers 23, 32 are connected two equal resistors 39, 70 which are in series. The output signals of the integrating inverting amplifiers 23, 32 can therefore be compared and the difference signal at the junction between resistors 39, 70 can then be amplified by amplifier 71. The output signal of the amplifier 71 is a steady DC voltage indicative of the actual temperature of the fluid 2.

For convenience of calibration, the output of amplifier 71 may be set to be zero DC output at a chosen reference temperature, typically 450°C for liquid sodium in a prototype fast reactor. The output of the amplifier 71 could be arranged to produce typically ± 12V DC when the sensor is surrounded by liquid sodium at temperatures ranging from 300° to 600°C that is to say ± 150°C about the reference temperature.

The device of FIG. 1 is incapable of distinguishing between changes in the electrical conductivity of the fluid 2 resulting from temperature, or flux distortion due to the flow of the conducting fluid. (The moving fluid distorts the magnetic flux pattern in the direction along the line of flow). The device of FIGS. 3 to 5, however, can be used to distinguish between temperature, or flow variations.

Figure 3:
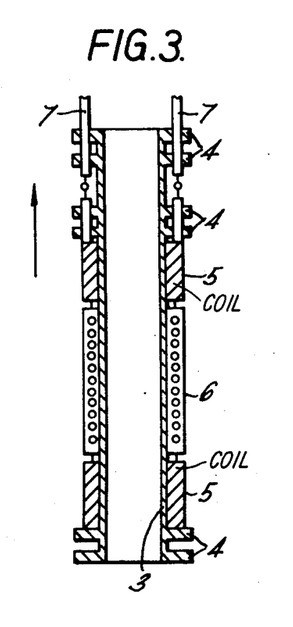
FIGS. 3 to 5 illustrate alternative forms of devices, constructed in accordance with the present invention, for indicating the temperature, and flow and temperature of an electrically conductive fluid.

Referring to FIG. 3, the device 1 is constructed in a similar manner to that of FIG. 1 except that the windings of coil 5 are split into two sections 5A, 5B (from the electrical point of view the coil 5 is still a single coil) and the coil 6 is located between each half of coil 5. Flux distortions due to the movement of fluid 2 tends to assist the coupling between one of the sections of coil 5 and the detection coil 6 whilst simultaneously reducing the coupling between the other section of coil 5 and the detection coil 6. In this way the flux distortion effects due to flow can be cancelled out automatically and the device becomes insensitive to flow. The device 1 of FIG. 3 can be further modified to enable temperature and flow information to be determined concurrently. To achieve this, the coil 6 may be provided with a centre tapped output (not shown) to provide effectively two coils 6A, 6B in a push-pull output configuration. In this way the signals due to different coupling conditions between coils 5 and 6 at each end of coil 5 may be used to provide an indication of the flow rate of fluid 2.

Figure 4:
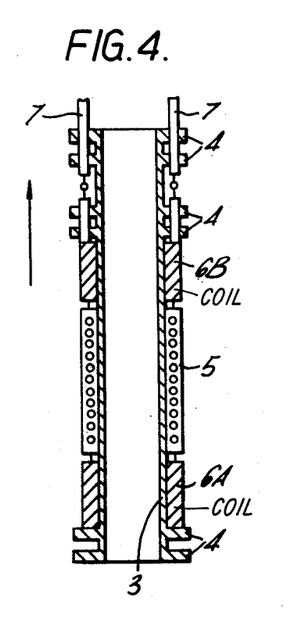

The device of FIG. 4 can be used to indicate temperature or flow variations of the fluid 2. The device of FIG. 4 is constructed in similar manner to that of FIG. 1 except that the windings of the detection coil 6 is split into two sections 6A and 6B instead of the coil 5. The flux distortions due to the movement of the fluid 2 tends to assist the coupling between the coil 5 and one of the sections 6A or 6B of coil 6 whilst simultaneously reducing the coupling between the other section of coil 6 and the coil 5. If one adds the outputs of both sections 6A and 6B of coil 6, then flux distortion effects due to flow are cancelled and the combined output is representative of temperature changes. On the other hand if the outputs of one section of coil 6 is subtracted from the output of the other section of coil 6 the difference signal is representative of the change in coupling between coils 5 and 6 due to flow.

Figure 5:
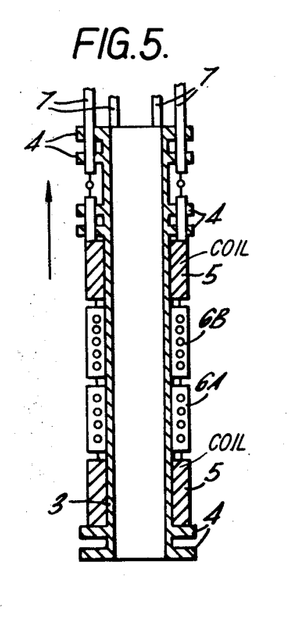

The device 1 may be constructed as shown in FIG. 5 to enable temperature or flow variations to be determined concurrently. Referring in greater detail to FIG. 5, the device 1 is constructed in a similar manner to the device of FIG. 1 except that the windings of the coil to be energised, coil 5, is split into two sections each of which is located at an end region of former 3, whilst two detection coils 6A, 6B are provided between the sections of coil 5. All the coils 5, 6A, 6B are mutually inductively coupled and are also inductively coupled by the fluid 2.

Figure 6:
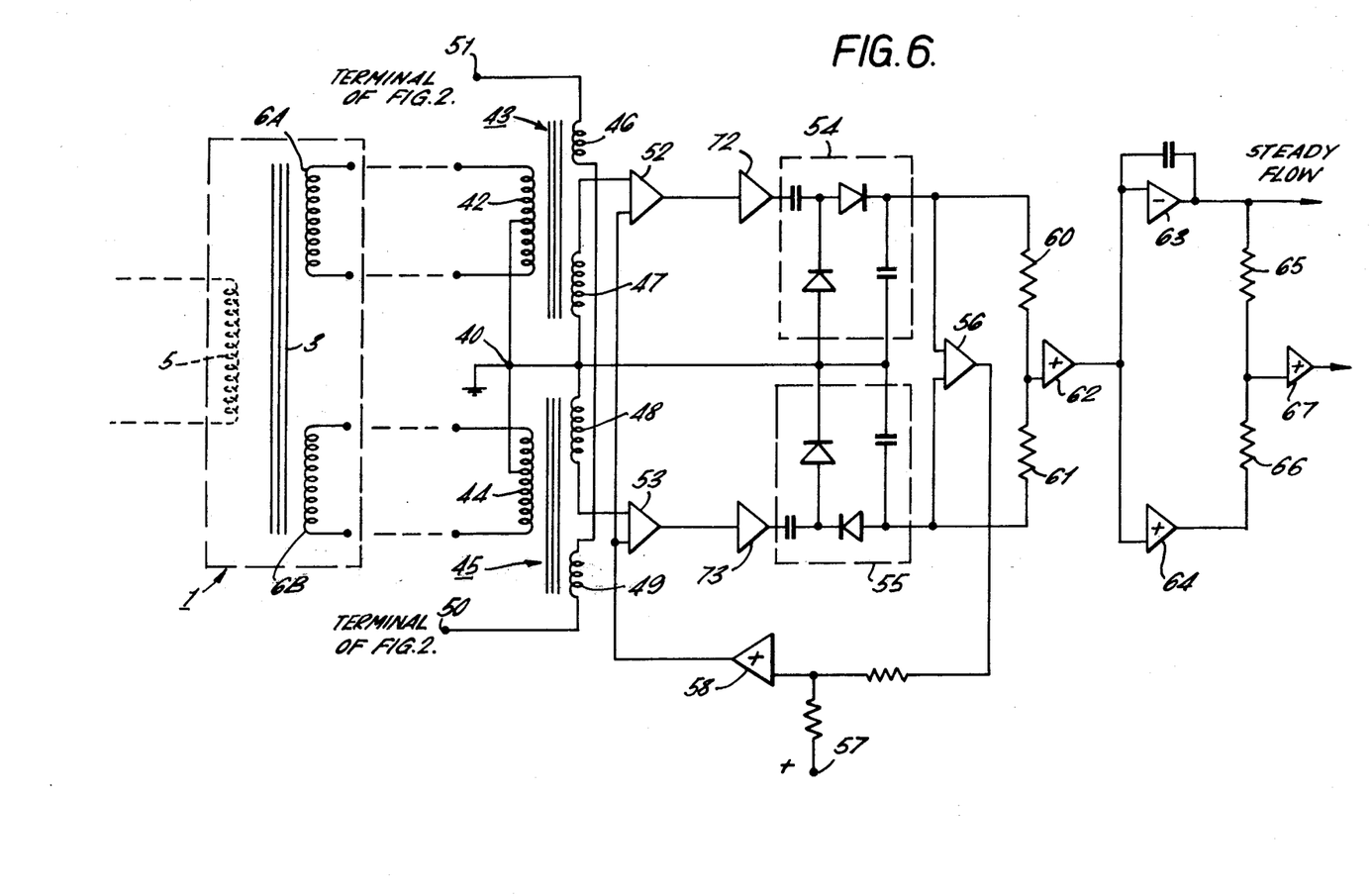
FIG. 6 is a circuit diagram of additional electronic circuits which are required for processing flow information from the detector coils of the devices of FIGS. 3 to 5.

An additional circuit diagram for use with the version of the device of FIG. 3 that has a centre-tapped output on coil 6, or the devices of FIGS. 4 and 5, to enable flow and temperature information to be determined concurrently is shown in FIG. 6. The coil 5 is energised in exactly the same way as shown in FIG. 2 and the current supplied to coil 5 is stabilised in exactly the same way using the same feed back loop (not shown in FIG. 6 but shown in FIG. 2). Coil 6A is connected to a balanced primary winding 42 of transformer 43 and coil 6B is connected to a balanced primary winding 44 of a transformer 45. In the case of the device of FIG. 3 with a centre tapped output on coil 6, the primary windings 42 and 44 of the transformers 43 and 45, instead of having centre tap outputs connected to the earth point 40 would be connected in series with the junction between them connected to the earth point 40.

Each transformer 43, 45 has two secondary windings 46, 47 and 48, 49 respectively. The secondary windings 46, 49 are connected in series and arranged so that their outputs add. There combined output is then fed to the detector circuits of FIG. 2 at terminals 50, 51. The transformer 13 of FIG. 2 is redundant since the transformers 43, 45 perform the function of transformer 13. The combined output signals of windings 46, 49 are processed by the circuit of FIG. 2, in exactly the same way as described above, to provide signals at the outputs of amplifiers 71 and 35 which are respectively representative of actual temperature of the fluid 2 and changes in temperature of the fluid about the mean temperature.

The secondary windings 47, 48 are also connected in series but their junction is connected to earth point 40 thus providing a push-pull input to two amplifier channels. The input signal to each channel is amplified by a variable gain controlled amplifier 52, 53 and the output signal from these amplifiers are further amplified by amplifiers 72, 73 and rectified by rectifier circuits 54, 55. The amplitude of the voltages induced in coils 6A, 6B will, by nature of the arrangement, vary proportional to the temperature of the fluid 2. Therefore the magnitude of any direct measurement of differences between the outputs of rectifier circuits 54, 55 for the purpose of flow determination will be affected by the temperature response of the system. If, however, the sum of the voltages induced in coils 6A, 6B (which is proportional to temperature ony), is compared with a reference voltage and the difference between the reference voltage and the sum of voltages from coils 6A, 6B used to control the gain of the amplifiers 52, 53, the outputs of the rectifiers 54, 55 can be normalised whilst still preserving the ratio between them. This normalising procedure is performed by the output signal of each rectifier circuit 54, 55 to a differential amplifier 56 where they are added. The output signal of the differential amplifier 56 is then compared with a reference voltage connected to terminal 57 and the difference signal, after being amplified by the amplifier 58 is used to control the amplification of amplifiers 52, 53. The reference voltage at terminal 57 is not necessarily the same as that connected to terminal 59 of the circuit of FIG. 2. The output signals of the rectifier circuits 54, 55 can be subtracted from each other. This is accomplished by connecting across the outputs of the rectifier circuits 54, 55 two equal resistors 60, 61. The difference signal, at the junction between resistances 60, 61, is amplified by the amplifier 62. The output signal from amplifier 62 is fed to the input of an inverting, integrating amplifier 63 and to the input of a non-integrating, non-inverting amplifier 64.

The output signal of amplifier 63 is a steady DC voltage indicative of a steady predetermined flow rate of fluid 2 whereas the output signal of amplifier 64 is a DC voltage which has superimposed on it a signal representative of short term fluctuations in the rate of flow of the fluid 2. By subtracting the signal from amplifier 63, from the output signal of amplifier 64 one may obtain a signal indicative of the variation of flow of the fluid 2. This is done by connecting two series connected resistors 65, 66 across the outputs of amplifiers 63, 64. The junction between the resistors is connected to the input of an amplifier 67. The signal appearing at the input of amplifier 67 is representative of the variation in flow of the fluid 2.

Typically the amplification of amplifier 63 would be set to produce between 1 and 2 volts output per meter per second flow of conductive fluid. The amplication of the flow variation channel (amplifier 67) would be typically 10 times greater than thatof 63. This would give a sensitivity of 10 to 20 volts per meter per second. Since in the signal processing, two DC signals are subtracted, signs are preserved and reversal of flow will produce a negative output voltage.

It has been found to be advantageous to employ a hollow core of Permendur V(Trade Mark) alloy inside the stainless iron former 3. In this way it has been possible to increase the range over which tempeprature can be measured up to about 930°C. The Permendur V alloy has a Curie Temperature point of 980°C.

During high temperature tests on a Permandur cored device, it was noticed that during heating and cooling cycles, there was a momentary change in the sensitivity of the device as the Curie point of the stainless iron former 3 was transversed. The recorded output voltage trace contained a small, but yet significant, blip at 705°C (typically a drop of 10%) on an otherwise smooth curve.

This effect may have use as a calibration marker for 705°C. Alternatively, if a material with a lower Curie point (about 400°C) were fitted inside the former 3 or the material from which the former 3 is made is changed, then a marker could be provided at the lower limit of the anticipated working range of temperature.

If the 'marker' effect is not wanted, then only one magnetic material must be used as the core of the device. The coil former could be made from Permendur V. However, since it is difficult material to machine, an easier solution is to fit a Permendur V liner inside the former 3 machined from non-magnetic stainless steel.

We claim:
1. The combination of a device for monitoring the electrical conductivity of an electrically conductive fluid and an electronic circuit for processing signals produced by the device, said device comprising at least first and second electrical coils for immersion in the fluid, said first coil constituting a coil to be energized with an alternating electrical current and said second coil constituting a detection coil for providing a signal representative of the electrical conductivity of the fluid, the first and second coils being wound on a common magnetic core and being arranged relative to each other so that, in use, said coils are mutually inductively coupled and are inductively coupled by the fluid; said electronic circuit comprising a source of electrical power for supplying electrical current to the first coil, means for generating an electrical reference signal with which the electrical current supplied to the first coil is compared, a feed back circuit, which is operative in response to variations from a predetermined relationship between the reference signal and the electrical current supplied to the first coil, for stabilizing the electrical current supplied to the first coil, and a comparator circuit for comparing the stabilized electrical current supplied to the first coil with the output signal of the second coil, the comparator circuit being operable to produce an output signal indicative of the inductive coupling between the first and second coils and hence the electrical conductivity of the fluid.

2. The combination according to claim 1 wherein the device further comprises a third coil wound on the magnetic core which is common to the first and second coils, the third coil constituting a second detection coil and the first coil being arranged co-axially with the second and third coils and being positioned therebetween.

3. The combination according to claim 1 wherein the device further comprises a third coil wound on the magnetic core which is common to the first and second coils, the third coil constituting a second coil to be energized, and the second coil being arranged co-axially with the first and third coils and being positioned between the first and third coils.

4. The combination according to claim 1 wherein the device further comprises third and fourth coils wound on to the magnetic core which is common to the first and second coils, the fourth coil constituting a second coil to be energized with an alternating current and the third coil constituting a second detection coil, the second and third coils being located side-by-side along the axis of said core and being positioned between the first and fourth coils.

5. The combination according to claim 1 wherein the feed-back circuit comprises means for deriving an alternating signal indicative of the current supplied to the first coil, a first rectifying circuit for rectifying the alternating signal which is indicative of the current supplied to the first coil, a first integrating amplifier for generating an output signal which is the integral of the output signal from the first rectifying circuit with respect to time, and a variable gain controlled amplifier which, in response to the output signal from the first integrating amplifier, is operative to adjust the current supplied to the first coil.

6. The combination according to claim 1 for monitoring the temperature of the fluid wherein the coils are mounted on a core which comprises a material the Curie point of which lies outside the range of temperatures to be monitored.

7. The combination according to claim 1 for monitoring the temperature of the fluid wherein the coils are mounted on a core which comprises a material the Curie point of which lies within the range of temperatures to be monitored so that the change of magnetic properties of the core when the fluid heats the core to its Curie point can be monitored to provide an indication that the fluid has reached a temperature sufficient to heat the core to the Curie point of the core.

8. The combination according to claim 3 wherein the electronic circuit includes two amplifier channels and the second and third coils are connected together so as to provide a push-pull input to the two amplifier channels, each of the amplifier channels comprising a variable gain controlled amplifier and a rectifier circuit for rectifying the output signal of the variable gain controlled amplifier, the second coil being connected to an input of one of the variable gain controlled amplifiers, the third coil being connected to an input of the variable gain controlled amplifier, and the output of each of the channels being connected to an input of a differential amplifier which is common to both channels and which is operative to compare the output signal of the channels and produce an output signal which is used to alter the gain of the variable gain controlled amplifier of each channel in response to the output signal of the differential amplifier.

9. The combination according to claim 2 wherein a second non-integrating amplifier is connected in parallel with the second integrating amplifier.

10. The combination according to claim 5, wherein the comparator circuit comprises, connected in electrical series circuit relationship, a second rectifying circuit for rectifying the output signal of the second coil, a second integrating amplifier for generating an output signal which is the integral of the output signal from the second rectifier circuit with respect to time, and a circuit for receiving the output signals from the first and second integrating amplifiers and for producing an output signal representative of the relationship between the current supplied to the first coil and the voltage induced in the second coil.

11. The combination according to claim 5 wherein a first non-integrating amplifier is connected in parallel with the first integrating amplifier.

12. The combination according to claim 11 wherein the said first integrating amplifier is an inverting amplifier and the said first non-integrating amplifier is a non-inverting amplifier.

13. The combination according to claim 11 wherein the said first integrating amplifier is a non-inverting amplifier and the said first non-integrating amplifier is an inverting amplifier.

14. The combination according to claim 9 wherein the said second integrating amplifier is an inverting amplifier and the said second non-integrating amplifier connected in parallel therewith is a non-inverting amplifier.

15. The combination according to claim 9 wherein the said second integrating amplifier is a non-inverting amplifier and the said second non-integrating amplifier connected in parallel therewith is an inverting amplifier.

16. The combination according to claim 9 wherein the electronic circuit includes means for comparing the output signals of the said first non-integrating amplifier and said first integrating amplifier with a signal representative of the difference between the output signals of the said second integrating amplifier and said second non-integrating amplifier connected in parallel with the second integrating amplifier, to produce an output signal representative of the relationship between changes of the current supplied to the first coil and changes of the signal produced by the second coil relative to predetermined mean values.

17. The combination according to claim 9 wherein the electronic circuit includes means for comparing the output signal of the second integrating amplifier with the output signal of the second non-integrating amplifier which is connected in parallel with the second integrating amplifier for providing an indication of the relationship between the mean level of the voltage induced in the second coil and fluctuations of the signal indicative of the voltage induced in the second coil.

18. The combination according to claim 9 wherein the electronic circuit includes means for comparing the output signal of the second first non-integrating amplifier with the output of the non-integrating amplifier connected in parallel with the second integrating amplifier for providing an indication of the relationship of variations of the current supplied to the first coil and variations of the output signal of the second coil.

19. The combination according to claim 8 wherein means are provided for generating a reference signal with which the output signal of the differential amplifier is compared, and means are provided for producing a signal, indicative of the difference between the reference signal and the output signal of the differential amplifier, which is used to control the gain of the variable gain controlled amplifier of each channel.

20. The combination according to claim 8 wherein the output signal of each channel is fed to a potential dividing circuit so that a signal indicative of the difference between the output signals of each channel is produced.

21. The combination according to claim 20 wherein the signal indicative of the difference between the output signals of each channel is fed to the input terminal of an integrating amplifier and a non-integrating amplifier.

22. The combination according to claim 21 wherein the output signal of the integrating amplifier and the output signal of the non-integrating amplifier are fed to a potential dividing circuit so that a signal representative of the difference between the output signals of the integrating and non-integrating amplifiers is produced.

* * * * *